(12) United States Patent
Gibson et al.

(10) Patent No.: US 8,404,255 B2
(45) Date of Patent: Mar. 26, 2013

(54) SYSTEM AND METHOD FOR TRANSDERMAL DRUG DELIVERY

(76) Inventors: Matt Gibson, Ann Arbor, MI (US); Takashi Yoshida Kozai, Ann Arbor, MI (US); Erin Purcell, Howell, MI (US)

( * ) Notice: Subject to any disclaimer, the term of this patent is extended or adjusted under 35 U.S.C. 154(b) by 889 days.

(21) Appl. No.: 12/334,379

(22) Filed: Dec. 12, 2008

(65) Prior Publication Data
US 2010/0028388 A1 Feb. 4, 2010

Related U.S. Application Data

(60) Provisional application No. 61/084,585, filed on Jul. 29, 2008.

(51) Int. Cl.
*A61K 9/00* (2006.01)
(52) U.S. Cl. ........................................ 424/400; 514/769
(58) Field of Classification Search ........................ None
See application file for complete search history.

(56) References Cited

U.S. PATENT DOCUMENTS

| | | | |
|---|---|---|---|
| 4,568,343 A | 2/1986 | Leeper et al. | |
| 5,601,839 A | 2/1997 | Quan et al. | |
| 5,879,326 A | 3/1999 | Godshall et al. | |
| 6,562,370 B2 * | 5/2003 | Luo et al. | 424/449 |
| 6,692,456 B1 | 2/2004 | Eppstein et al. | |
| 7,611,481 B2 * | 11/2009 | Cleary et al. | 604/46 |
| 2003/0060479 A1 * | 3/2003 | Brown et al. | 514/282 |
| 2005/0181029 A1 * | 8/2005 | Mitragotri et al. | 424/448 |

OTHER PUBLICATIONS

Chapter 5 of Transdermal Drug Delivery System (Doctoral Dissertation of Niclas Roxhed (2007).*
Freedictionary.com entry for "microscale chemistry." Accessed at <http://www.thefreedictionary.com/Microscale+chemistry> on Aug. 21, 2012.*
Muragan, Ramalingam and Ramakrishna, Seeram, "Nano-Featured Scaffolds for Tissue Engineering: A Review of Spinning Methodologies," Tissue Engineering, Mar. 31, 2006, vol. 12(3), pp. 435-447, Mary Ann Liebert, Inc. publishers. USA.
Jones, Richard., "What is this thing called nanotechnology? Part 1. The Nano-scale." http://www.softmachines.org/wordpress/?p=21. Published Sep. 22, 2004. Accessed Apr. 19, 2012.

* cited by examiner

*Primary Examiner* — David J Blanchard
*Assistant Examiner* — Garen Gotfredson (57) ABSTRACT

In the preferred embodiment, the invention is a system for creating micropores in the skin for transdermal drug delivery through the micropores and includes: a chemical that dissolves or breaks down superficial layers of skin; a chemical delivery element that holds and delivers controlled volumes of the chemical to skin, creating micropores; and a base that is able to temporarily couple to skin, contains the chemical delivery elements, and may activate the chemical delivery elements to administer the chemical to skin. In the preferred embodiment, the invention is a method for delivering drugs transdermally that includes providing a carrier containing a chemical delivery element with a chemical to break down superficial layers of skin; placing the carrier into contact with skin; activating the chemical delivery element; allowing the chemical to break down superficial layers of skin and creating micropores; and providing a drug to be delivered transdermally through the micropores.

33 Claims, 8 Drawing Sheets

FIG. 15

SYSTEM AND METHOD FOR TRANSDERMAL DRUG DELIVERY

CROSS-REFERENCE TO RELATED APPLICATIONS

This application claims the benefit of U.S. Provisional Application No. 61/084,585, filed on 29 Jul. 2008, which is incorporated in its entirety by this reference.

TECHNICAL FIELD

This invention relates generally to the drug delivery field, and more specifically to an improved system and method for transdermal drug delivery and the method of making this improved system.

BACKGROUND

Over 10% of the population has a phobia of needles, which has created a growing $6 billion market for drug delivery through the skin. Although some drugs (most notably nicotine and birth control) are available for skin delivery, most drugs are large molecules that will not pass through the skin on their own. Penetration through the stratum corneum, or outermost layer of the skin, is a significant challenge of transdermal drug delivery, particularly for macromolecules (MW>1 kDa). Conventional approaches to transdermal drug delivery of macromolecules include iontophoresis, microneedles, electrical microporation, lasers, and ultrasound. However, there are several key factors that are preventing them from being widely commercially used. Transdermal delivery systems such as radiofrequency micro-ablation, ultrasound, lasers, and electrical microporation require expensive, heavy, and bulky electronics that are impractical for common, everyday use. Additionally microneedles often require a high-speed injector device, have a low penetration rate, and frequently break causing the delivery system to fail and leaving shards in the skin. Thus, there is a need for an improved system and method for transdermal drug delivery. This invention provides such an improved and useful system and method for transdermal drug delivery and a method of making this improved system.

DESCRIPTION OF THE PREFERRED EMBODIMENTS

The following description of preferred embodiments of the invention is not intended to limit the invention to these embodiments, but rather to enable any person skilled in the art to make and use this invention.

Figure 1:
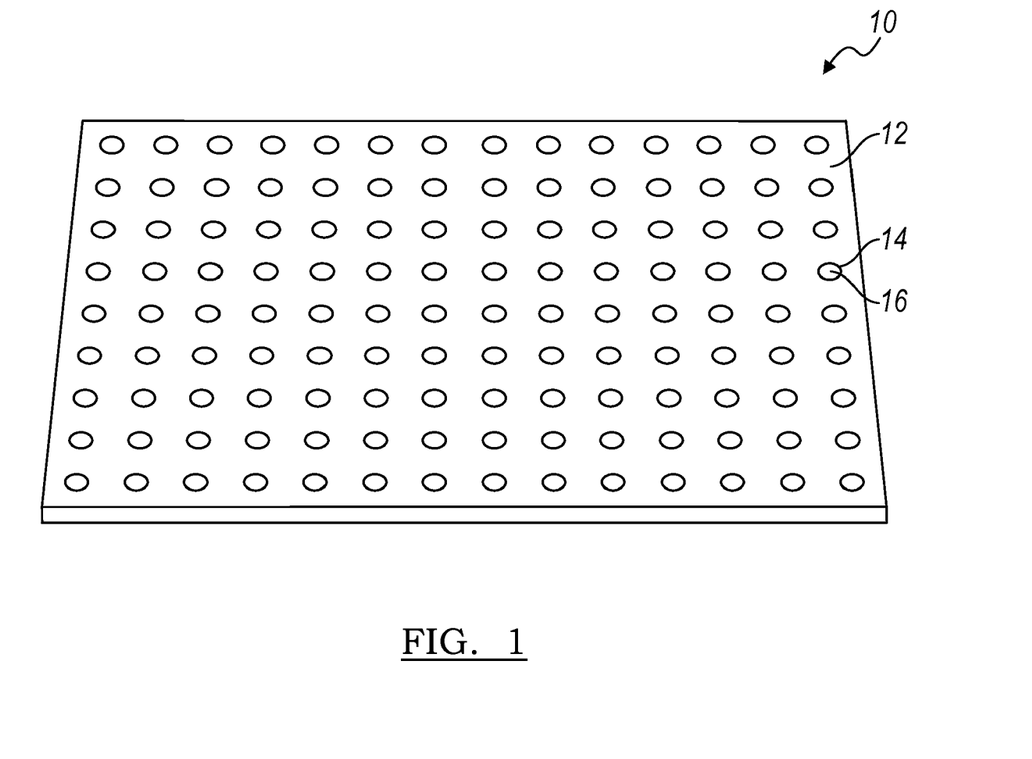
FIGS. 1-3 are representations of the system of the first preferred embodiment of the invention.
Figure 2:
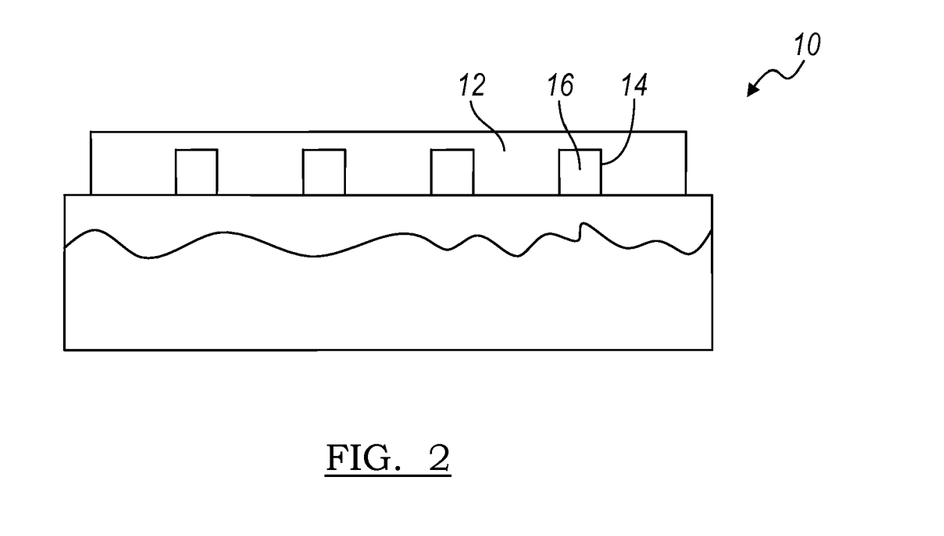
Figure 3:
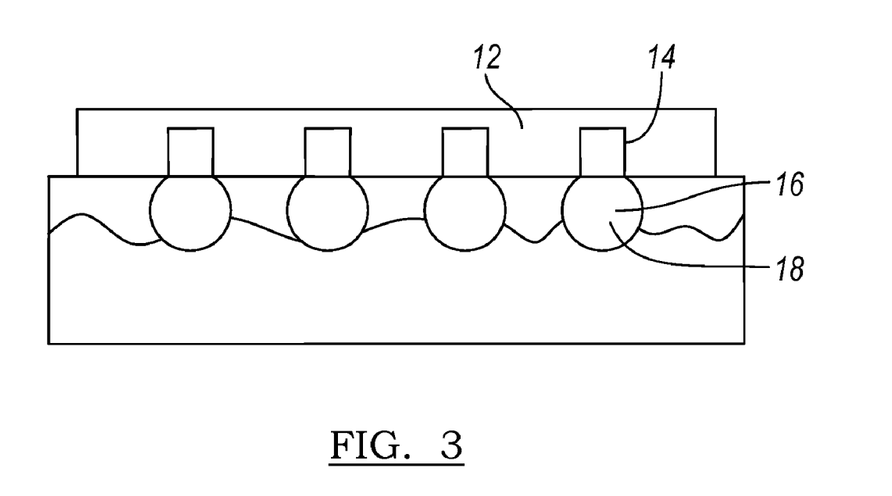
Figure 4:
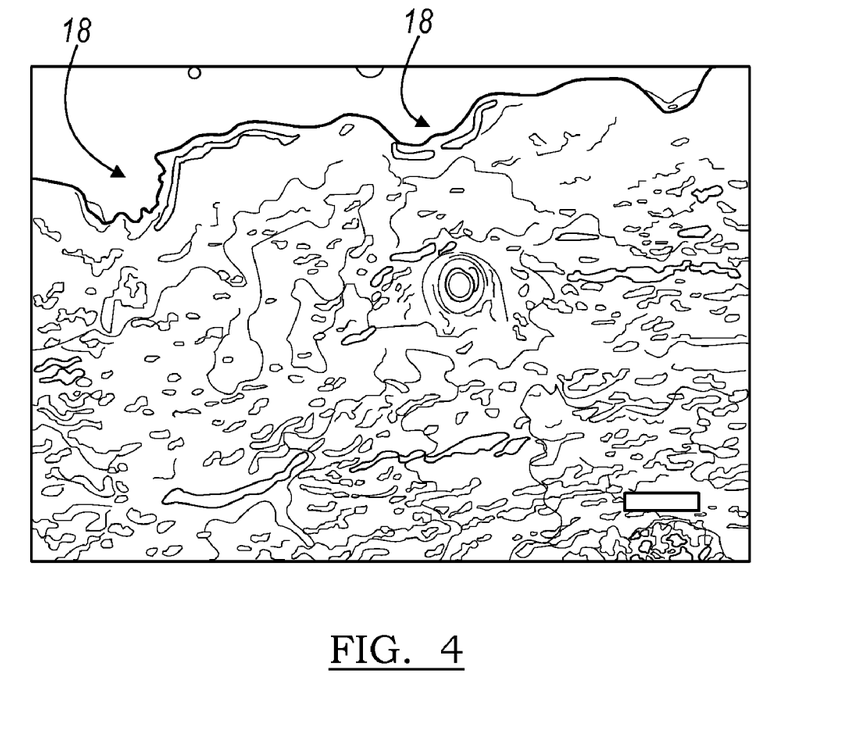
FIG. 4 is an image of a skin sample with micropores (stained with Masson's trichrome, Scale=200 μm)

As shown in FIGS. 1 and 2, the system 10 of the preferred embodiments includes a chemical 16, a series of chemical delivery elements 14 that hold and deliver the chemical 16, and a base 12 that contains the chemical delivery elements 14. When the base 12 is coupled to an outer layer of skin of a patient, the chemical delivery elements 14 are activated and function to deliver the chemical 16 to the outer layer of skin of the patient (the stratum corneum). The chemical 16 functions to create a series of micropores 18, as shown in FIGS. 3 and 4, in the outer layer of skin of the patient. Because nerve endings do not reach the outer layer of skin, the patient does not feel pain from the creation of the micropores 18. The system 10 of the preferred embodiment is preferably designed to enable transdermal drug delivery, and more specifically, to create a series of micropores 18 in an outer layer of skin of the patient. The micropores 18 preferably increase skin permeability of the patient, enabling a drug 22 (shown in FIG. 5) to reach the body of the patient. The system 10 of the preferred embodiments, however, may be alternatively used in any suitable environment and for any suitable reason.

1. The System

Figure 5:
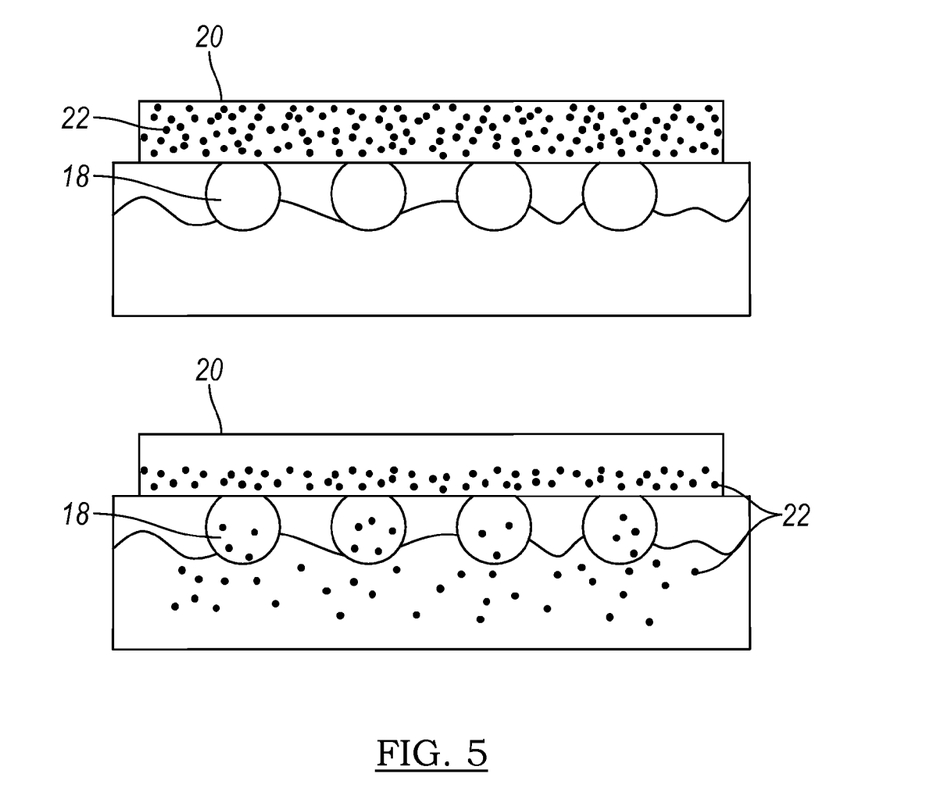
FIG. 5 is a representation of transdermal drug delivery enabled by the system of the preferred embodiment of the invention.

As shown in FIGS. 3-5, the chemical 16 of the preferred embodiments functions to create a series of micropores 18 in the outer layer of skin (the stratum corneum) of the patient, which preferably increase skin permeability of the patient and enable a drug 22 to reach the body of the patient. The chemical 16 is preferably an agent that does not pose a threat if it is taken up by the vasculature and/or deposited in another location in the body of the patient. The chemical 16 is preferably one of several suitable agents such as acids, bases, lipid, and/or enzymes, but may alternatively be any other suitable chemical to dissolves, or otherwise breaks down, the skin and to create micropores 18 in outer layer or stratum corneum of the skin. In a first variation, the chemical 16 is preferably 10N potassium hydroxide (10N KOH), but may alternatively be any other concentration up to approximately 10N of potassium hydroxide. Although 10N KOH is relatively strong, the combination of the small volume held by each chemical delivery element and the small area of skin that the chemical 16 is contacting enables the chemical 16 to form precise micropores 18 in the superficial layers of the skin. In addition, as the chemical 16 diffuses through the skin and creates the micropores, the chemical 16 is subsequently diluted and loses its original ability to break down tissue such as vaculature or nerves once it has gone past the superficial layers of the skin. In alternative variations, the chemical 16 is preferably an acid such as Hydrochloric acid (HCl), a base such as Sodium hydroxide (NaOH), an enzyme such as papain, bromelain, actinidin, ficin, or any other suitable agent such as Esters.

As shown in FIG. 5, the micropores 18 created by the chemical are preferably spaced such that they produce microscale, invisible channels into the skin through which drug molecules may diffuse or pass. The creation of the micropores 18 by the chemical 16 is preferably pain free and invisible to the eye. The micropores 18 are preferably in the range of approximately 10 µm to 300 µm in diameter, but may alternatively be of any appropriate size to allow a macromolecular drug (preferably greater than 1 kDa) to diffuse through the outer layer of skin, while at the same time small enough such that the skin of the patient can naturally heal and/or close the pores.

As shown in FIG. 1, the series of chemical delivery elements 14 of the preferred embodiments functions to hold and deliver the chemical 16 to the outer layer of skin of the patient. The series of chemical delivery elements 14 preferably function to focus a series of small volumes of a chemical 16 to a portion of the outer layer of skin of the patient. Each chemical delivery element 14 is preferably on the order of 100 µm by 100 µm, but may alternatively have any other suitable dimension. The dimensions of the chemical delivery element 14 may also be specific to the drug 22 that is to be delivered by the system. To prevent overlap of the created micropores 18 because of diffusion of the chemical 16 through the skin, each chemical delivery element 14 is preferably spaced at least 50 µm (center to center) from one another. In the preferred embodiments, each chemical delivery element 14 is preferably spaced about 500 µm (center to center) from one another, but may alternatively have any other suitable spacing. Each chemical delivery element 14 preferably holds a volume of 0.5 to 2.5 nL of the chemical 16, but may alternatively hold any other suitable amount of chemical appropriate to create the desired micropores 18 while accommodating for variation in thicknesses of the superficial layers of skin. The series of chemical delivery elements 14 preferably holds a total volume of the chemical 16 of about 1 µL, but may alternatively hold a volume approximately of the range from 0.1 µL to 100 µL. However, the series of chemical deliver elements 14 may hold any other total volume suitable for creating miropores over the area necessary to transmit an appropriate dosage of transdermal drug 22.

The series of chemical delivery elements 14 is preferably one of several variations. In a first variation, as shown in FIGS. 2 and 3, the series of chemical delivery elements 14 is a series of wells that function to hold a volume of the chemical 16. Each well is preferably cube-shaped, 100 µm×100 µm horizontally and about 250 microns deep, but may alternatively have any suitable geometry of any suitable dimension. The material of the series of wells is preferably the same material a material that may be made temporarily hydrophilic and is otherwise hydrophobic. The material is preferably a polymer such as Polydimethylsiloxane (PDMS), which is a hydrophobic material that can be made temporarily (less than 30 minutes) hydrophilic when exposed to oxygen plasma. This property enables the wells to be loaded with the chemical 16. A vacuum may be used to facilitate filling the wells with the chemical 16. When the hydrophobic property of the material of the wells returns, it will form a tight interface between the chemical 16 and the wells, such that the chemical does not spill outside of the well. The hydrophobic property of the material also facilitates the deposition of chemical 16 onto the skin upon application to the skin. Alternatively, a vacuum may be used to fill the wells without using oxygen plasma. However, any other suitable method for loading the delivery elements 14 with the chemical 16 may be used.

Figure 6:
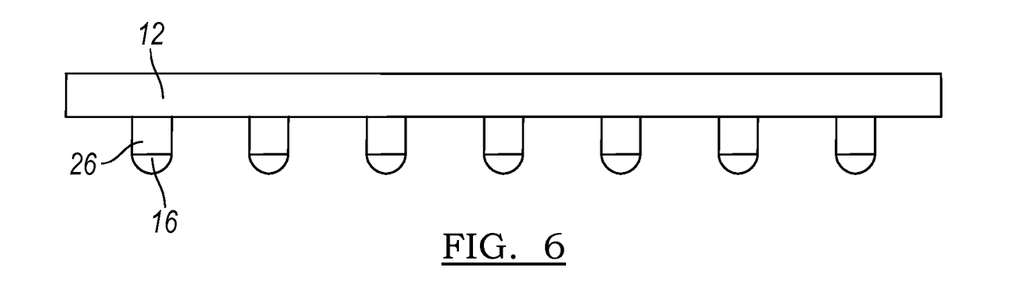
FIGS. 6 and 7 are representations of variations of the first embodiment in FIGS. 1-3.
Figure 7:
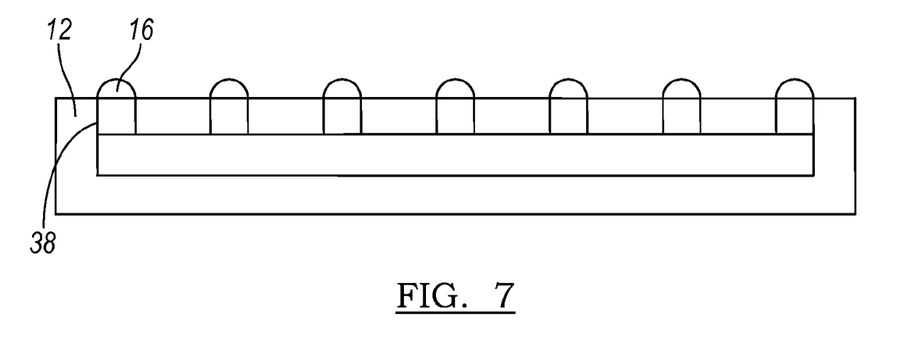
Figure 8:
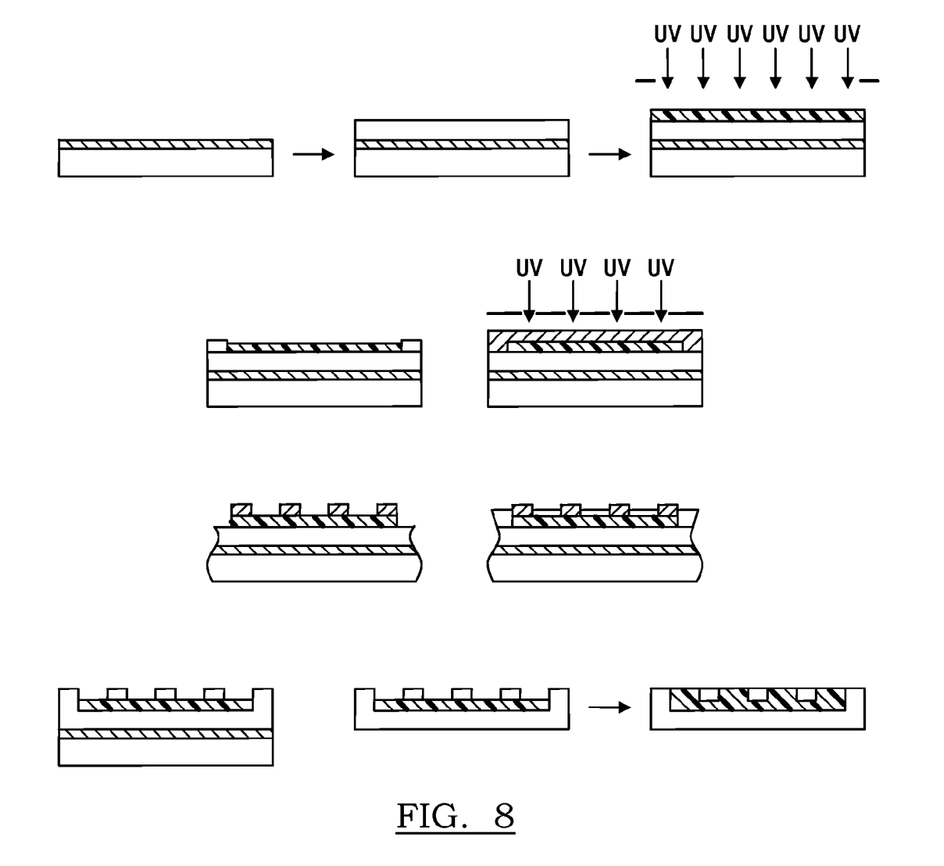
FIG. 8 is a representation of the method of making the system of the variation of the first preferred embodiment in FIG. 7.

In a second variation, as shown in FIG. 6, the series of chemical delivery elements 14 is a series of columns 26 that function to hold the chemical 16 such that when the base 12 is coupled to the outer layer of skin of the patient, the columns 26 function to deliver the chemical 16 to the outer layer of skin of the patient by "stamping" the chemical 16 onto the skin. In a third variation, as shown in FIG. 7, the series of chemical delivery elements 14 is a series of electrode sites 38, electrochemically coated with a polymer having the chemical 16. When the base 12 is coupled to the outer layer of skin of the patient, the chemical 16 will preferably leech out of the polymer coating into the outer layer of skin of the patient. The coating is preferably a thin coating, preferably on the order of 50 µm, but may alternatively be any other suitable thickness. The series of chemical delivery elements of this variation is preferably fabricated as shown in FIG. 8, but may alternatively be fabricated in any other suitable fashion. Although the series of chemical delivery elements 14 is preferably one of these three variations, the series of chemical delivery elements 14 may be any suitable element to hold and deliver a chemical 16.

As shown in FIGS. 1 and 2, the base 12 of the preferred embodiments includes the series of chemical delivery elements 14 and functions to couple to an outer layer of skin of a patient. When coupled to the skin of the patient, base 12 functions to activate the delivery elements 14 to deliver the chemical 16. The base 12 is preferably of the same material as the chemical delivery elements 14 and is preferably made of a polymer such as Polydimethylsiloxane (PDMS), but may alternatively be made of any suitable material. The material of the base 12 is preferably inert and non-toxic, such that it is biocompatible. The base 12 is preferably removably fixable to the skin. The base 12 preferably includes an adhesive that is removably fixable to the skin, but may alternatively be removably fixable to the skin in any other suitable fashion. The base 12 preferably has dimensions of about 5 cm×5 cm×1 cm, and more preferably has dimensions of less than 2 cm×2 cm×0.5 cm, but may alternatively have any other dimension suitable to enable the appropriate dose of drug 22 to be delivered transdermally to the body.

Figure 9:
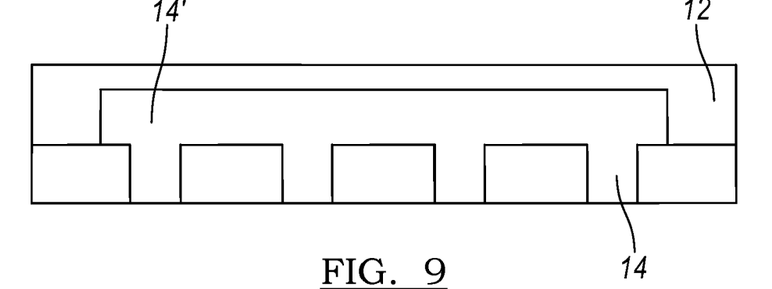
FIGS. 9, 10, and 11 are representations of the system of the second, third, and fourth preferred embodiments of the invention, respectively.

As shown in FIG. 9, the system 10 of the second embodiment is nearly identical to the system 10 of the first embodiment. The difference between the two embodiments, however, is that the system 10 of the second embodiment further includes a chemical reservoir 14'. In this embodiment, the chemical reservoir 14' preferably includes an additional volume of the chemical 16, which can ensure that the system 10 includes enough volume of the chemical 16 to create appropriately sized micropores 18. The chemical reservoir 14' preferably holds an additional total volume of chemical 16 of about 30 to 50 µL, but may alternatively hold any other suitable total volume.

Figure 10:
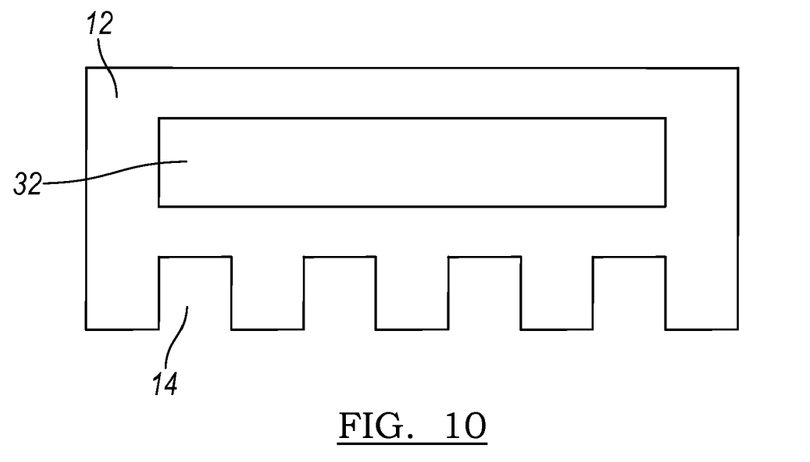
Figure 11:
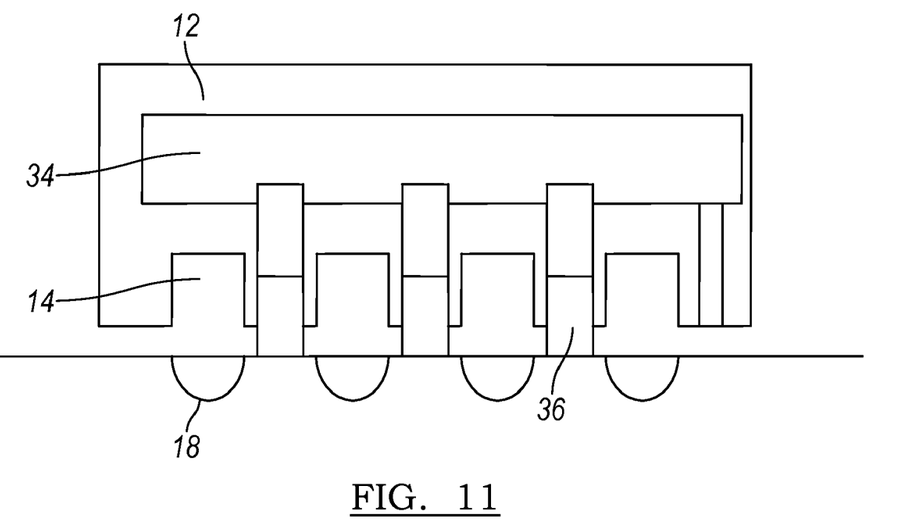
Figure 12:
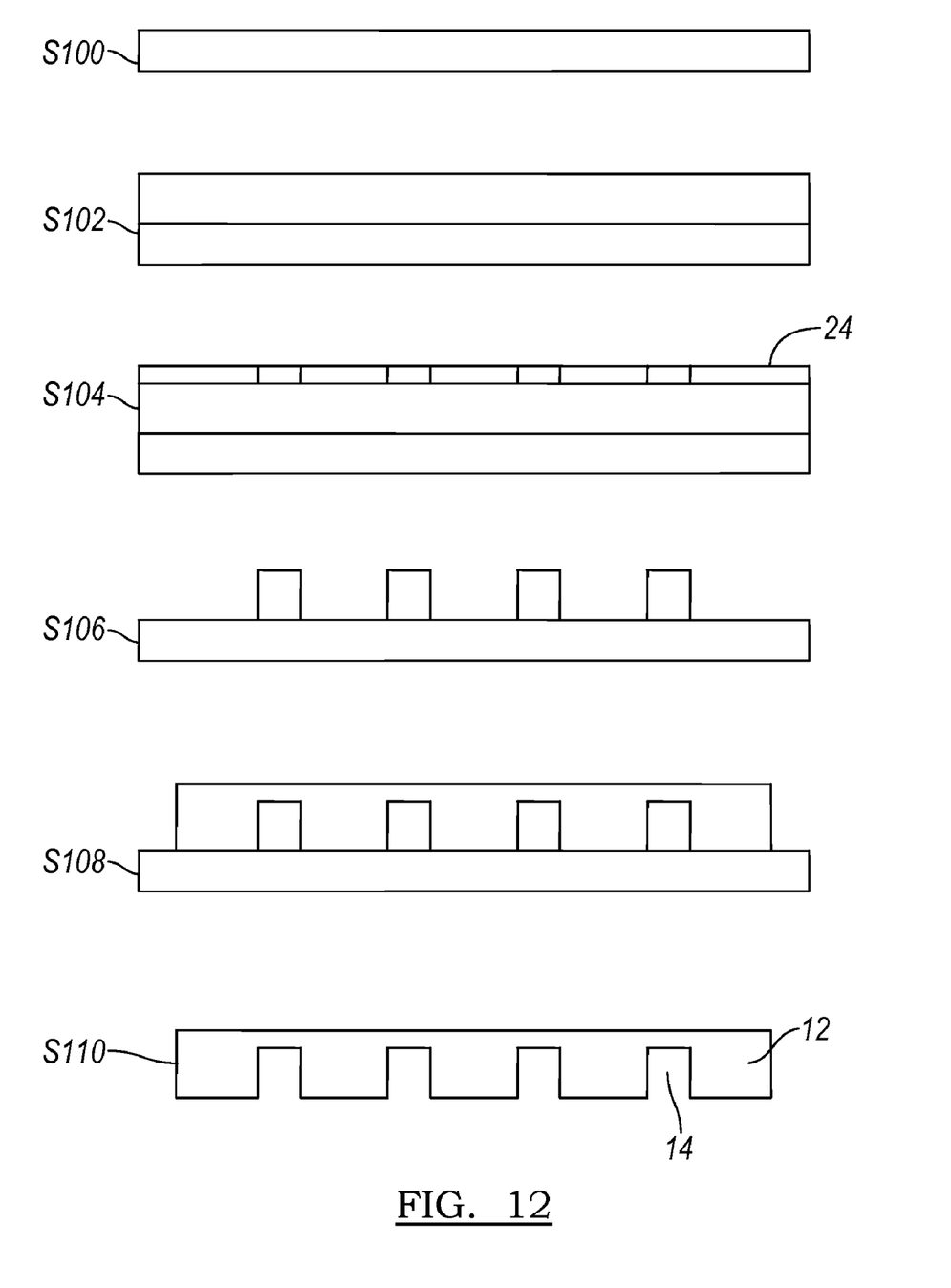
FIG. 12 is a representation of the method of making the system of the preferred embodiment of the invention.
Figure 13:
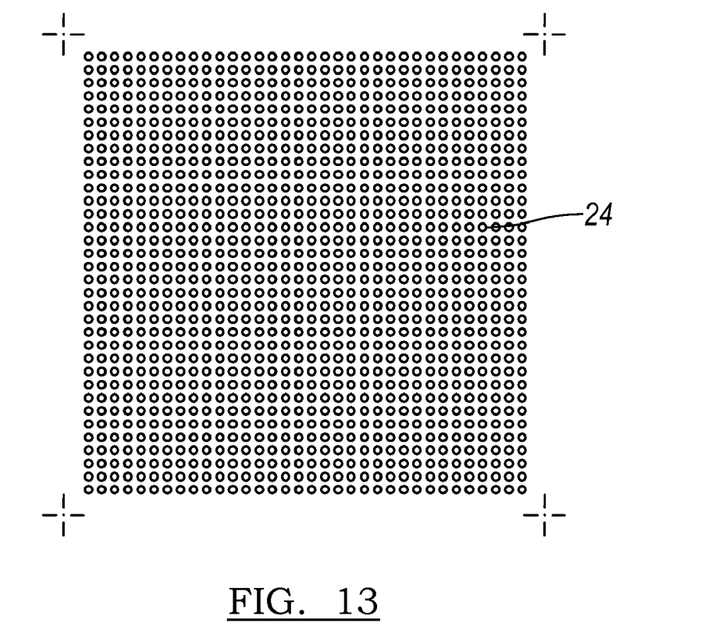
FIG. 13 is a representation of the mask used in the method of making the system of the preferred embodiment of the invention.
Figure 14:
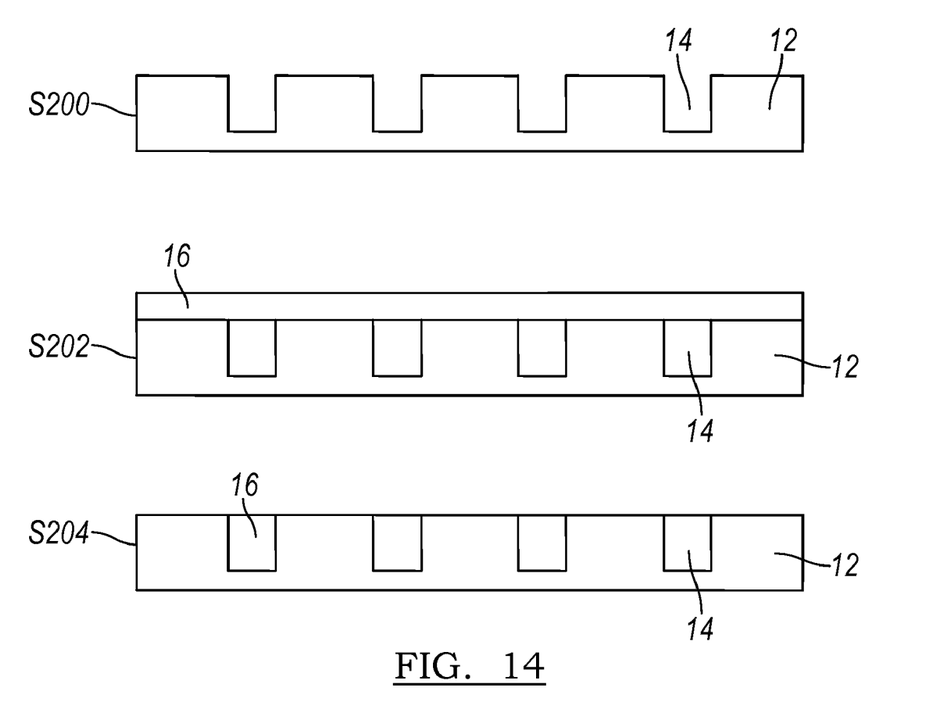
FIG. 14 is a drawing of the method of adding a chemical to the system of the preferred embodiment of the invention.
Figure 15:
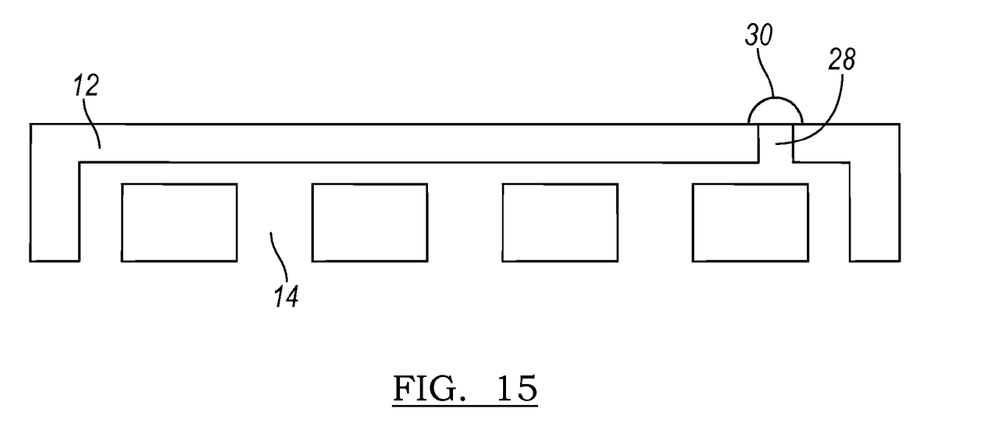
FIG. 15 is a drawing of an alternate method of adding a chemical to the system of the preferred embodiment of the invention.

As shown in FIG. 10, the system 10 of the third embodiment is nearly identical to the system 10 of the first embodiment. The difference between the two embodiments, however, is that the system 10 of the third embodiment further includes a hydration reservoir 32. In this embodiment, the hydration reservoir 32 preferably maintains the hydration level of the chemical 16, which can prevent dehydration of the chemical 16 after the system has been packaged and while it is being stored. This arrangement may be quite useful in certain environments, such as to increase the "shelf life" of the system 10.

As shown in FIG. 5, the system 10 of the preferred embodiments also includes a drug delivery element 20. The drug delivery element 20 functions to hold a drug 22 and functions to deliver a drug 22 to the micropores 18 created in the outer layer of skin of the patient. The drug delivery element 20 is preferably any suitable drug infused patch that functions to hold a drug 22 and functions to deliver a drug 22 to the skin. The drug 22 is preferably any suitable drug and more preferably any suitable macromolecular drug that functions to enter a patient's body through a series of micropores 18 created by the system 10. One specific example of a suitable drug is botulinum toxin, or Botox. Other examples of suitable drugs include Enoxaparin (Lovenox), Caspofungin (Cancidas), Etanercept (Enbrel), Somatostatin (Sandostatin), or any other high molecular weight pharmaceuticals. The drug 22 may further include a buffer to neutralize the chemical 16 in the body of the patient before the drug 22 enters the body of the patient.

As shown in FIG. 11, the system 10 of the fourth embodiment is nearly identical to the system 10 of the first embodiment. The difference between the two embodiments, however, is that the system 10 of the fourth embodiment further includes a drug reservoir 34, that functions to store and deliver drug 22, and at least one pillar 36 that functions to simultaneously lift the base 12 off of the surface of the skin and compress the drug reservoir 34 such that the drug 22 exits the drug reservoir 34. In this embodiment, the chemical 16 is preferably applied to the skin to create the series of micropores 18. The pillars 36 are then activated such that they lift the base 12 off of the surface of the skin and compress the drug reservoir 34. The pillars are preferably activated by gas expansion. The gas expansion may be activated by the user, but may also be an automatic gas expansion that expands at a rate that allows the chemical delivery elements 14 to administer the appropriate amount of the chemical 16 for the appropriate length of time before fully lifting the base 12 off the surface of the skin. However, the pillars may alternatively be activated by any other suitable mechanism. Once the base 12 is lifted off the surface of the skin, and the drug 22 exits the drug reservoir 34, the drug 22 preferably seeps below the lifted patch and enters the micropores 18 in the skin. The drug 22 in this embodiment preferably includes a buffer to neutralize the chemical 16 in the body of the patient before the drug 22 enters the body of the patient. The system 10 may alternatively include a drug reservoir 34 that supplies the drug 22 to the micropores 18 in any other suitable arrangement.

2. Method of Making the System

The system 10 of the preferred embodiment is preferably micro-machined using standard microfabrication techniques, but may alternatively be fabricated in any other suitable fashion. As shown in FIG. 12, the method of the preferred embodiments includes the steps of providing a wafer S100, building up the mold material S102, masking a portion of the mold material S104, removing a portion of the mold material S106, adding the base material to the mold S108, and removing the base 12, which has a series of chemical delivery elements 14, from the mold S110. The method is preferably designed for the manufacture of system 10 for transdermal drug delivery. The method, however, may be alternatively used in any suitable environment and for any suitable reason.

One specific example of the method of the preferred embodiments uses photolithography or photolithographic patterning to create the mold. In Step S100, a bare silicon wafer is first cleaned in acetone and isopropyl alcohol (IPA) to remove any organics or surface impurities. AP300 is then preferably spun onto a clean four-inch wafer at 500 rpm for 5 seconds, followed immediately by 4000 rpm for 30 seconds. AP300 functions to improve SU8 adhesion. In Step S102, the mold material, SU8-2075 (Microchem Corp.), is preferably spun onto the wafer. The thickness of the mold material is preferably of 250 μm, but may alternatively be any other suitable thickness. The mold material is preferably SU-8, but may alternatively be any other suitable material, which functions well with the chosen material for the base 12. The spread cycle in this variation preferably lasts 12 seconds at 500 rpms (a=100 rpm/s) while the spin cycle is preferably 1,200 rpm spin for 30 seconds (a=300 rpm/s). After settling for 30 minutes, the wafer is preferably soft baked initially at 65° C. for 7 minutes followed immediately by a second bake at 95° C. bake for 45 minutes. Deep edge bead removal is then preferably performed by washing the edge of the wafer with ACS soaked 10 mm brush while the wafer was spinning at 500 rpm. The edge is then preferably cleaned with developer while the wafer is preferably spun at 500 rpm. In Step S104, a mask 24 is preferably applied to the surface of the wafer using a glass sheet. As shown in FIG. 13, a specific example of the mask 24 is a square grid of 25 by 25 chemical delivery elements over a 1.4 cm×1.4 cm area. Each chemical delivery element is 100 μm width and 100 μm height with 500 μm spacing (center-to-center). The mask 24 may alternatively have any other suitable geometry with any other suitable dimensions. The mask 24, on the mold material, is then preferably exposed for 15 seconds with 60 second pauses, repeated 5 times for an approximate total exposure of approximately 450 mJ/cm2 and put through a post exposure bake at 65° C. for 5 minutes, immediately followed by at 95° C. for 15 minutes. In Step S106, the excess mold material is removed by soaking the wafer in developer for 17 minutes with agitation, and, after removing the wafer, it is preferably sprayed by a developer for 10 seconds, then IPA for 10 seconds, followed by a rinse with di$H_2$O. After air-drying the wafer, it is preferably hard baked at 150° C. for 5 minutes to prepare the mold. The patterned SU-8 layer then preferably serves as a mold for the base 12, as shown in step S108 in FIG. 12. The mold is then preferably incubated in a chamber with 1 ml of methyltrichlorosilane for 30 minutes at room temperature. The material for the base 12 is then preferably prepared by mixing pre-polymer and curing agent in a 10:1 ratio. The mixture is degassed in a vacuum changer to remove bubbles for 30 minutes, and then poured onto the wafer without forming bubbles. The wafer is then baked at 80° C. for 30 minutes. However, any other suitable process may be used to create a mold and the base 12.

As shown in FIG. 14, the base 12, removed from the mold, is preferably plasma oxidized, making it hydrophilic (Step S200). Step S202 shows the chemical 16 deposited over the surface of the base 12 and chemical delivery elements 14. In S204, a vacuum is preferably applied to fill the chemical delivery elements with the chemical 16. As shown in FIG. 15, the system 10 may alternatively be filled with the chemical 16 by use of a channel system 28 such that the chemical 16 may be inserted into the base 12 from the opposite side of the chemical delivery elements 14. In this variation, oxygen plasma may be similarly used to make the chemical delivery elements 14 and channel system 28 to be hydrophilic and a vacuum is then preferably applied to fill the channel system 28 and the chemical delivery elements 14 with the chemical 16. Once the chemical 16 is inserted into the base 12, and the chemical delivery elements 14 are filled with the chemical 16, the channel system 28 is preferably sealed with any suitable cap or sealant 30. In both variations, a vacuum may be used alone to fill the chemical delivery elements 14 (and the channel system 28) without the assistance of oxygen plasma. However, any other suitable type of method or catalyst for filling the chemical delivery elements 14 with chemical 16 may be used.

Although omitted for conciseness, the preferred embodiments include every combination and permutation of the various bases 12, chemical delivery elements 14, chemicals 16, drug delivery elements 20, drugs 22, and methods of making these elements.

As a person skilled in the art will recognize from the previous detailed description and from the figures and claims, modifications and changes can be made to the preferred embodiments of the invention without departing from the scope of this invention defined in the following claim.

We claim:

1. A system for delivering a drug through the skin of a user comprising:
   a chemical that, when delivered to the skin of the user, increases the permeability of the skin;
   a plurality of chemical delivery elements, wherein the plurality of chemical delivery elements are wells having dimensions of approximately 25-100 μm×25-100 μm, and wherein each of the plurality of chemical delivery elements retains a volume of the chemical for delivery to the skin; and
   a base that contains the plurality of chemical delivery elements, and wherein the plurality of chemical delivery elements deliver the volume of the chemical to the skin when the base is coupled to the skin, thereby forming a plurality of micropores in the skin corresponding to the plurality of chemical delivery elements.

2. The system of claim 1 wherein the chemical is selected from the group consisting of acids, bases, lipids, and enzymes.

3. The system of claim 2 wherein the chemical is potassium hydroxide.

4. The system of claim 2 wherein the chemical is selected from the group consisting of hydrochloric acid (HCl), sodium hydroxide (NaOH), papain, bromelain, actinidin, ficin, and esters.

5. The system of claim 1 wherein the system includes a volume approximately of the range 0.1 μL to 100 μL of the chemical.

6. The system of claim 1 wherein the chemical delivery elements are each of a cube shaped well with dimensions approximately 100 μm×100 μm in a plane parallel to the skin and approximately 250 μm in a direction perpendicular to the skin.

7. The system of claim 1 wherein the chemical delivery elements each hold approximately 0.5 nL to 2.5 nL of the chemical.

8. The system of claim 1 wherein the chemical delivery elements are arranged in an array.

9. The system of claim 8 wherein the chemical delivery elements are each spaced such that the center of each chemical delivery element is at least about about 50 μm apart from a neighboring chemical delivery element.

10. The system of claim 1 wherein the chemical delivery elements are of a material that may be made temporarily hydrophilic to accept the chemical and is otherwise hydrophobic to allow release of the chemical to the skin.

11. The system of claim 10 wherein the material is Polydimethylsiloxane (PDMS).

12. The system of claim 1 further comprising a chemical reservoir that contains an additional volume of the chemical, wherein each of the chemical delivery elements are in communication with the chemical reservoir.

13. The system of claim 1 further comprising a hydration reservoir containing a hydrator that maintains the hydration level of the chemical while in the system.

14. The system of claim 1 wherein the material of the base is the same as the material of the chemical delivery elements.

15. The system of claim 1 wherein the base has dimensions of approximately 5 cm×5 cm×1 cm.

16. The system of claim 1 further comprising a drug to be delivered transdermally through the micropores.

17. The system of claim 16 wherein the drug contains neutralizers to neutralize the chemical upon application of the drug to the skin.

18. The system of claim 16 further comprising a drug delivery element that holds and delivers a volume of the drug through the micropores.

19. The system of claim 18 further comprising columns that raise the chemical delivery elements away from the skin and compress the drug delivery element to deliver the drug to the skin.

20. The system of claim 19 wherein the columns are activated by gas expansion.

21. The system of claim 16 wherein the drug is a macromolecular drug.

22. A system for delivering a drug through the skin of a user comprising:
   a chemical that, when delivered to the skin of the user, increases the permeability of the skin;
   a plurality chemical delivery elements, wherein each of the plurality of chemical delivery elements retains a volume of the chemical for delivery to the skin, the volume being approximately 0.5 nL to 2.5 nL; and
   a base that contains the plurality of chemical delivery elements, and wherein the plurality of chemical delivery elements deliver the volume of the chemical to the skin when the base is coupled to the skin, thereby forming a plurality of micropores in the skin corresponding to the plurality of chemical delivery elements.

23. The system of claim 22 wherein the chemical is selected from the group consisting of acids, bases, lipids, and enzymes.

24. A method for delivering a drug through the skin of a user comprising the steps of:
   providing a chemical delivery system, wherein the system comprises:
   a plurality of chemical delivery elements, wherein the plurality of chemical delivery elements are wells having dimensions of approximately 25-100 μm ×25-100 μm, and wherein each of the plurality of chemical delivery elements retains a volume of a chemical that, when delivered to the skin of the user, increases the permeability of the skin; and
   a base that contains the plurality of chemical delivery elements;
   placing the base on the skin, such that the plurality of chemical delivery elements contact the skin; and
   delivering the volume of the chemical to the skin, thereby forming a plurality of micropores in the skin.

25. The method of claim 24 further comprising delivering a drug on the skin having micropores, whereby at least a portion of the drug diffuses through the micropores.

26. The method of claim 25 wherein the drug is a macromolecular drug.

27. The method of claim 24 wherein the chemical is selected from the group consisting of acids, bases, lipids, and enzymes.

28. The method of claim 24 wherein the plurality of micropores correspond to the plurality of chemical delivery elements.

29. The method of claim 28 wherein the chemical delivery elements are shaped as wells.

30. The method of claim 28 wherein the chemical delivery elements are shaped as columns.

31. The system of claim 1 wherein the base has dimensions no greater than approximately 2 cm ×2 cm ×0.5 cm.

32. The system of claim 22 further comprising a drug to be delivered transdermally through the micropores.

33. The system of claim 32 wherein the drug is a macromolecular drug.

* * * * *